(12) United States Patent
Fiechter et al.

(10) Patent No.: US 10,631,901 B2
(45) Date of Patent: Apr. 28, 2020

(54) DEVICE FOR IMPLANTING A SURGICAL SCREW

(71) Applicant: MEDACTA INTERNATIONAL SA, Castel san Pietro (CH)

(72) Inventors: Meinrad Fiechter, Lugano (CH); Alfonso Fantigrossi, Turate (IT); Francesco Siccardi, Vico Morcote (CH)

(73) Assignee: MEDACTA INTERNATIONAL SA, Castel san Pietro (CH)

( * ) Notice: Subject to any disclaimer, the term of this patent is extended or adjusted under 35 U.S.C. 154(b) by 80 days.

(21) Appl. No.: 15/128,564

(22) PCT Filed: Mar. 24, 2015

(86) PCT No.: PCT/IB2015/052135
§ 371 (c)(1),
(2) Date: Sep. 23, 2016

(87) PCT Pub. No.: WO2015/145343
PCT Pub. Date: Oct. 1, 2015

(65) Prior Publication Data
US 2018/0008318 A1    Jan. 11, 2018

(30) Foreign Application Priority Data
Mar. 26, 2014    (IT) .............................. M12014A0513

(51) Int. Cl.
*A61B 17/70*    (2006.01)
*A61B 17/86*    (2006.01)
(Continued)

(52) U.S. Cl.
CPC ........ *A61B 17/708* (2013.01); *A61B 17/7076* (2013.01); *A61B 17/862* (2013.01);
(Continued)

(58) Field of Classification Search
CPC ............ A61B 17/7032; A61B 17/7034; A61B 17/7037; A61B 17/708; A61B 17/7082;
(Continued)

(56) References Cited

U.S. PATENT DOCUMENTS 7,648,521 B2    1/2010  Hestad
7,666,189 B2 *  2/2010  Gerber ............... A61B 17/7074
                                                        606/104

(Continued)

FOREIGN PATENT DOCUMENTS

EP         2705799        12/2014
JP        2006504505       2/2006
(Continued)

*Primary Examiner* — Kevin T Truong
*Assistant Examiner* — Tracy L Kamikawa
(74) *Attorney, Agent, or Firm* — Allen, Dyer, Doppelt + Gilchrist, P.A.

(57) ABSTRACT

A device may include an outer sleeve with a hollow interior, and an inner sleeve with a hollow interior to couple axially and slidingly. The outer sleeve may include an outer central body, an outer proximal end part and an outer distal end part integrally connected to one another, and an outer channel extending along the entire outer proximal end part and along a substantial portion of the outer central body. The inner sleeve may include an inner central body, an inner proximal end part and an inner distal end part integrally connected to one another, and an inner channel extending along the entire inner proximal end part and along a substantial part of the inner central body. The inner sleeve may include, in the inner proximal end of the inner sleeve, a lateral engagement element, and an axial engagement element for releasably engaging a surgical screw.

18 Claims, 10 Drawing Sheets

(51) Int. Cl.
*A61B 17/88* (2006.01)
*A61B 17/00* (2006.01)

(52) U.S. Cl.
CPC ...... *A61B 17/8891* (2013.01); *A61B 17/7032* (2013.01); *A61B 17/7037* (2013.01); *A61B 2017/00477* (2013.01); *A61B 2017/00991* (2013.01)

(58) Field of Classification Search
CPC .............. A61B 17/862; A61B 17/8891; A61B 2017/00477; A61B 2017/00991; A61B 17/7076
See application file for complete search history.

(56) References Cited

U.S. PATENT DOCUMENTS

| | | | |
|---|---|---|---|
| 7,749,233 B2 | 7/2010 | Farr et al. | |
| 7,854,751 B2* | 12/2010 | Sicvol | A61B 17/7032 606/246 |
| 8,038,699 B2* | 10/2011 | Cohen | A61B 17/7085 606/246 |
| 8,246,659 B2 | 8/2012 | Vonwiller et al. | |
| 8,292,896 B2 | 10/2012 | Abdou | |
| 8,439,922 B1* | 5/2013 | Arnold | A61B 17/7082 606/86 A |
| 8,945,183 B2 | 2/2015 | Altarac et al. | |
| 9,017,411 B2 | 4/2015 | Crawford | |
| 9,198,698 B1* | 12/2015 | Doose | A61B 17/7089 |
| 9,282,979 B2 | 3/2016 | ONeil et al. | |
| 9,320,550 B2 | 4/2016 | Hutton et al. | |
| 9,326,798 B2* | 5/2016 | Kolb | A61B 17/7076 |
| 9,375,240 B2 | 6/2016 | McBride et al. | |
| 9,861,399 B2 | 1/2018 | Rogers et al. | |
| 9,907,581 B2 | 3/2018 | Hess | |
| 10,194,952 B2 | 2/2019 | Ramsay et al. | |
| 2005/0131408 A1* | 6/2005 | Sicvol | A61B 17/7032 606/86 A |
| 2005/0215999 A1 | 9/2005 | Birkmeyer et al. | |
| 2006/0074445 A1* | 4/2006 | Gerber | A61B 17/7074 606/191 |
| 2006/0111715 A1* | 5/2006 | Jackson | A61B 17/861 128/897 |
| 2006/0217712 A1 | 9/2006 | Mueller et al. | |
| 2007/0129731 A1* | 6/2007 | Sicvol | A61B 17/7032 606/104 |
| 2008/0021454 A1 | 1/2008 | Chao et al. | |
| 2008/0021455 A1 | 1/2008 | Chao et al. | |
| 2008/0125788 A1 | 5/2008 | Cohen et al. | |
| 2008/0234738 A1 | 9/2008 | Zylber et al. | |
| 2008/0287981 A1 | 11/2008 | Culbert et al. | |
| 2009/0005813 A1 | 1/2009 | Crall et al. | |
| 2009/0143828 A1* | 6/2009 | Stad | A61B 17/7085 606/86 A |
| 2010/0312279 A1* | 12/2010 | Gephart | A61B 17/3421 606/264 |
| 2011/0077690 A1 | 3/2011 | Shin et al. | |
| 2012/0016422 A1 | 1/2012 | Hua | |
| 2013/0144349 A1 | 6/2013 | Corin | |
| 2014/0031873 A1 | 1/2014 | Jackson | |
| 2014/0039567 A1* | 2/2014 | Hoefer | A61B 17/708 606/86 A |
| 2014/0052180 A1* | 2/2014 | Justis | A61B 17/7032 606/246 |
| 2014/0052187 A1 | 2/2014 | McBride et al. | |
| 2018/0303625 A1 | 10/2018 | Alheidt et al. | |

FOREIGN PATENT DOCUMENTS

| | | |
|---|---|---|
| JP | 2011072772 | 4/2011 |
| WO | 2004041100 | 5/2004 |
| WO | 2010030916 | 3/2010 |

\* cited by examiner

DEVICE FOR IMPLANTING A SURGICAL SCREW

RELATED APPLICATION

This application is based upon prior filed copending International Application No. PCT/IB2015/052135 filed Mar. 24, 2015, which claims priority to Italian Application No. MI2014A000513, filed Mar. 26, 2014, the entire subject matter of which is incorporated herein by reference in its entirety.

TECHNICAL FIELD

The present disclosure relates to a medical device, and more particularly, to a device for implanting a surgical screw and related methods.

BACKGROUND

In the state of the art, a variety of systems and techniques are known to intervene on specific problems of the spine, such as abnormal curvature of the spine, injuries to the same, etc. The intervention on these types of spine-specific problems frequently requires the stabilization of a portion of the spine portion so as to facilitate the fusion of two or more vertebrae together in a single bone agglomeration.

This type of intervention is frequently employed for the correction of many pathological conditions of the spine such as, for example, degenerative diseases of the bone disc elements, scoliosis, spinal stenosis, or the like. Not infrequently, these corrective measures require the use of implants, such as, for example, bone grafts. The stabilization of the spine allows the creation of a bone tissue in the intervertebral part; in this way, a part of the spine is fused into a single bone body.

The stabilization of the spine is a known technique, and a variety of methods and devices have been developed for the correction of many pathologies that affect characteristically this body part in order to stabilize its configuration, facilitating the vertebral fusion at various levels. One of these known systems provides that a bar is arranged longitudinally along the portion of the spine which needs the intervention. This bar is shaped in such a way as to represent the correct anatomical shape which is characteristic of that specific portion of a healthy spine.

With this method, therefore, the bar is positioned along the spine to engage various vertebrae, as needed. It should be noted that, typically, in this type of surgery, two parallel bars are used that are arranged at the sides of the central area of the spine. Therefore, during the surgery, the pair of bars is fixed to the spine by means of various fixing means, including, for example, screws. These screws are attached to the bone structure, typically to the vertebral pedicle.

The inclination of the bar and, consequently, the positioning of the fixing screws varies depending on the type of correction to be done and, of course, from vertebra to vertebra. It seems clear that for a successful surgery, the procedure needs to properly fix both the corrective bar and the screws. In order to obtain a correct positioning of the elements, according to the needs of the patient, polyaxial screws are utilized.

The implant of the polyaxial screws, bars and any necessary fixing means, may require typically somewhat invasive interventions resulting in injuries to the skin and muscle tissues of the patient. This surgery may require rather long hospitalization and rehabilitation times.

In order to reduce the invasiveness of the surgery, the operative technique was directed toward minimally invasive techniques able to significantly reduce the trauma to the tissues, with benefits for the patient including, for example, shorter hospitalization times, lower postoperative pain, less rehabilitation, and with benefits for the hospitals, including shorter hospitalization times, fewer costs, and fewer resources for the rehabilitation. To address the needs of this type of minimally invasive interventions, instruments capable of allowing the surgeon to secure the polyaxial screws in the desired position have been developed, also through an incision of limited size on the patient's body, along with the possibility of implanting the bars in the desired position through the instruments.

An example of this type of surgery instruments is illustrated in the U.S. Patent Application Publication No. 2013/0144349 to Lanx Inc., Broomfield, Colo. (USA). This approach discloses an instrument to facilitate minimally invasive surgery procedures. The instrument comprises an outer sleeve, in turn comprising a first and a second elongated sleeve, each having a distal end and a proximal end. The inner sleeve has a first and a second channel extending between the first and the second elongated sleeve, starting from the distal end. The first and the second channel each have a length greater than the half of the total length of the first and second elongated sleeve. The outer sleeve includes a third and fourth elongated sleeve, each having a proximal and a distal end, the outer sleeve also comprises a third and a fourth channel extending between the third and the fourth elongated sleeve, starting from the distal end. The third and fourth channel each have a length greater than the half of the length of the third and fourth elongated sleeve. In that instrument, the inner sleeve is dimensioned in such a way as to be housed inside the outer sleeve. The instrument comprises a connecting element adapted to couple the two proximal ends of the first and second elongated sleeve with the proximal ends of the third and fourth elongated sleeve. It is also provided an alignment element to align the first channel with the third channel and the second channel with the fourth channel, when the inner sleeve is housed inside the outer sleeve. Additionally, the device has coupling means with an implant, these being adapted to secure the first and the second sleeve to the implant in a demountable manner.

SUMMARY

Generally speaking, a device is for implanting a surgical screw. The device may include an outer sleeve with a hollow interior, and an inner sleeve with a hollow interior to couple axially and slidingly. The outer sleeve may include an outer central body, an outer proximal end part and an outer distal end part integrally connected to one another, and an outer channel extending along the entire outer proximal end part and along a substantial portion of the outer central body. The inner sleeve may include an inner central body, an inner proximal end part and an inner distal end part integrally connected to one another, and an inner channel extending along the entire inner proximal end part and along a substantial part of the inner central body. The inner sleeve may include, in the inner proximal end of the inner sleeve, a lateral engagement element, and an axial engagement element for releasably engaging a surgical screw.

DETAILED DESCRIPTION

However, the prior art suffers from a number of drawbacks. As known in the art, in fact, the polyaxial screw is first engaged from the side by the outer sleeve and only thereafter by the inner sleeve. This asynchrony just described results in a lack of stability of the connections between the device known in the art and the polyaxial screw, with consequent problems during the phases of surgery.

In addition, the length of the channels present in the device as found in U.S. Patent Application Publication No. 2013/0144349 makes the device poorly resistant to the bending stresses. In fact, if the device is in the closed configuration and is coupled with a polyaxial screw, for example, during minimally invasive surgery, it is possible that the user, for example the surgeon engaged in the surgery procedure, may inadvertently apply a bending stress by simply tilting the distal part of the device with respect to its central axis. In this case, the proximal part of the internal and external sleeves, both of which are integral with the polyaxial screw, undergoes a bending resulting in a risk that the proximal part of the outer sleeve will decouple from the proximal part of the inner sleeve of the device, thus leading to the accidental opening of the known device and to the decoupling of the same from the polyaxial screw. This accidental decoupling can, in certain cases, lead to the undesired injury of the patient and the incorrect positioning of the surgical screw, with also relevant consequences for the success of the procedure. A further drawback of current approaches may be the labor needed to implant typical devices.

An object of the present disclosure is to provide a device for implanting a surgical screw that is capable of coupling with the screw in a simple and quick way. Another object of the present disclosure is to provide a device for implanting a surgical screw that is able to withstand the bending, torsion and traction stresses, without being disunited or decoupled from the surgical screw. Further object of the present disclosure is to provide a device as specified which is easy to use, fast to use, robust, and that has a low cost.

Figure 1:
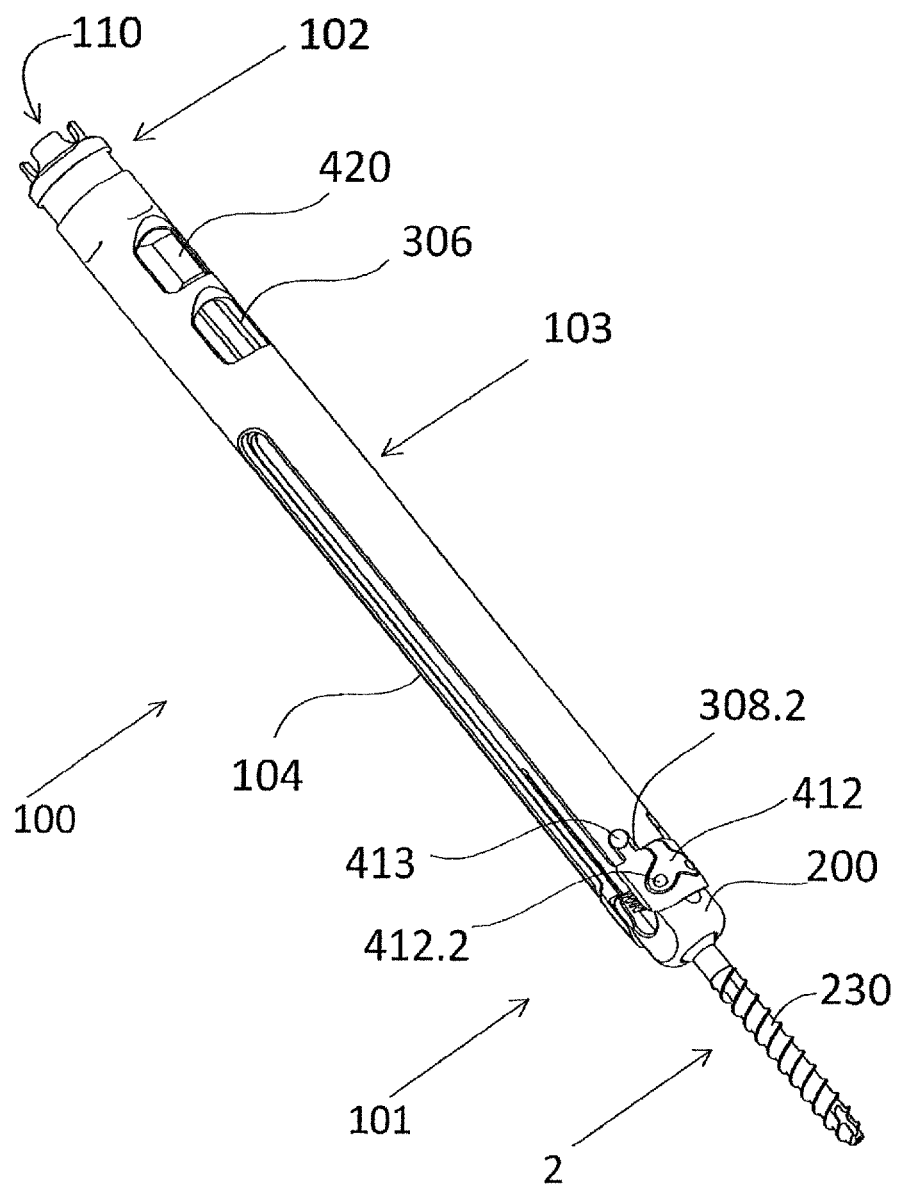
FIG. 1A is an elevational side front view of the device for implanting a surgical screw in the closed configuration with an assembled polyaxial screw of the present invention.
FIG. 1B is a side front elevational view of the device for implanting a surgical screw in the open configuration with an assembled polyaxial screw of the present invention.
Figure 1B:
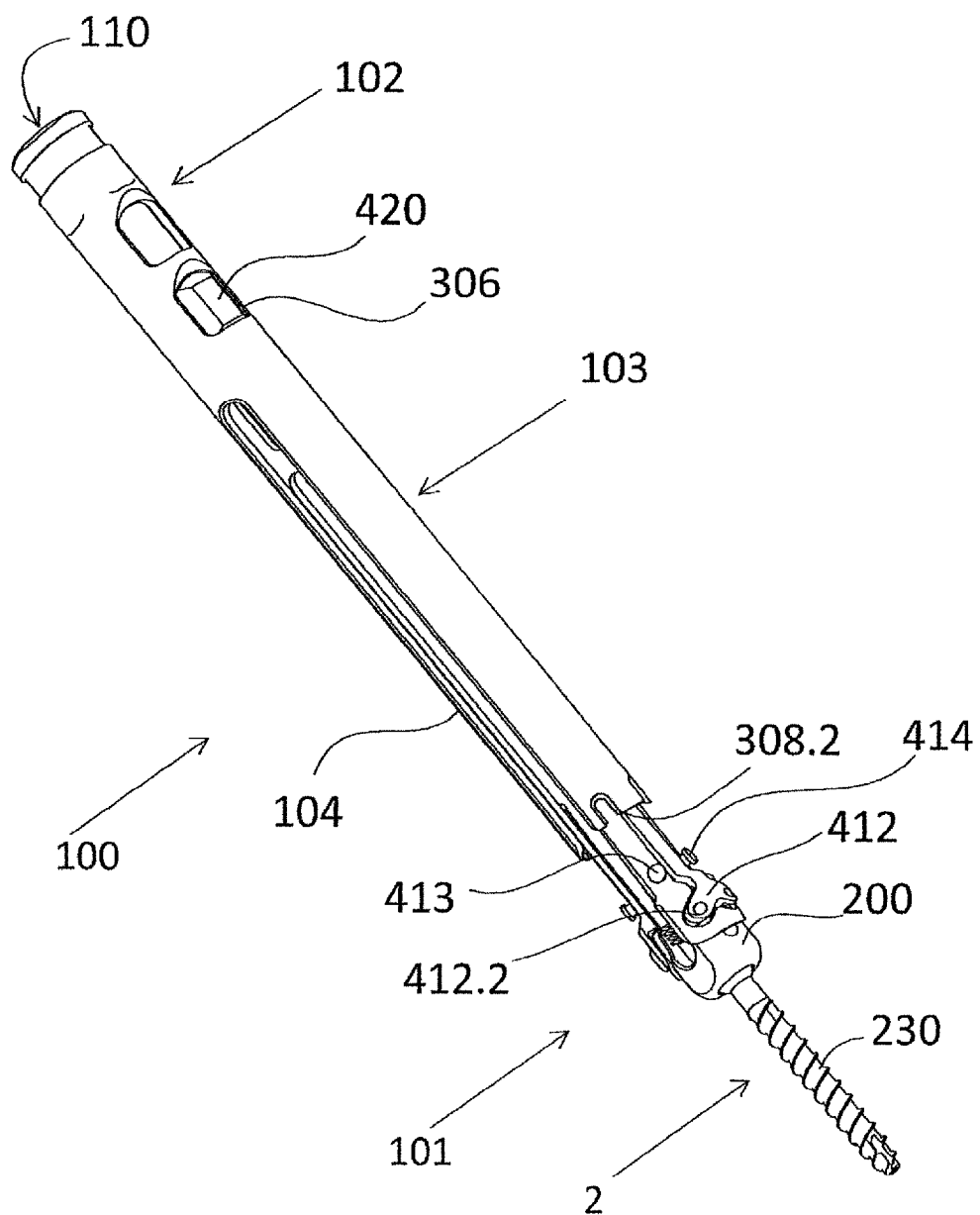

With reference to FIGS. 1A-8B, a device for implanting a surgical screw is now described. FIGS. 1A-1B are an overall view of the device 100 for implanting a surgical screw in the closed configuration. It has a substantially cylindrical shape with vertical axis, a hollow interior, having a greater dimension extending in the axial direction. Again in the axial direction, it is possible to identify two end parts: a first end part 101, the proximal part, has a substantially circular hollow section with a open bottom sleeve and communicating with the internal cavity of the device body 100, and is adapted, by coupling means, to be coupled to a surgical screw, for example, a polyaxial screw 2, while a second end part 102, the distal part, has a circular hollow section with an open top 110, is configured for a comfortable grip by the user and has, in a part thereof, a command, for example a button 420. Along substantial part of the device 100 for implanting a surgical screw 2, there are two channels 104 (FIG. 1A) and 105 (FIG. 6) passing through and extending from the proximal end 101 for a substantial part of the axial dimension of the device 100.

Figure 2:
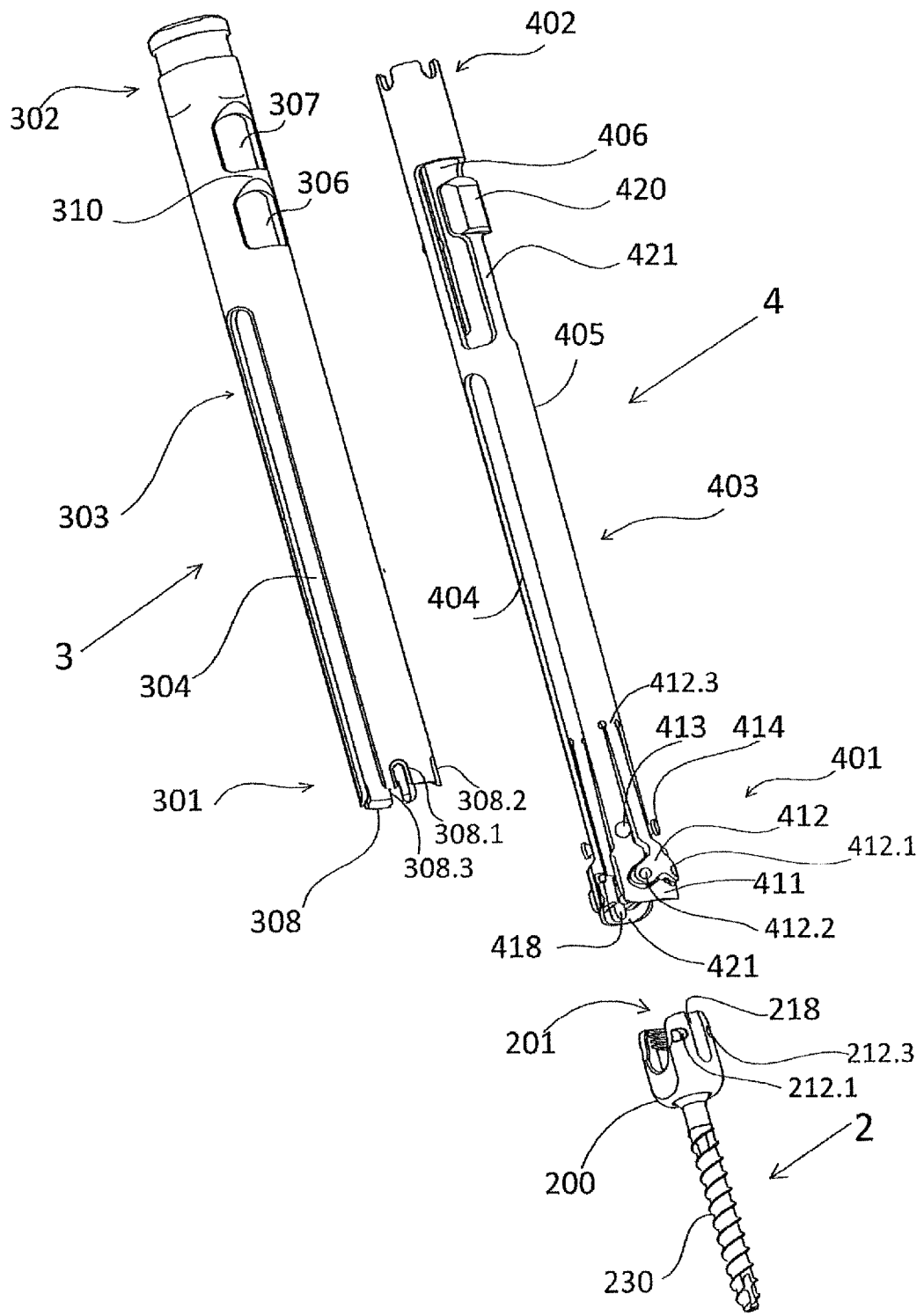
FIG. 2 is a side front elevational view of the device for implanting a surgical screw in the disassembled configuration.
Figure 3A:
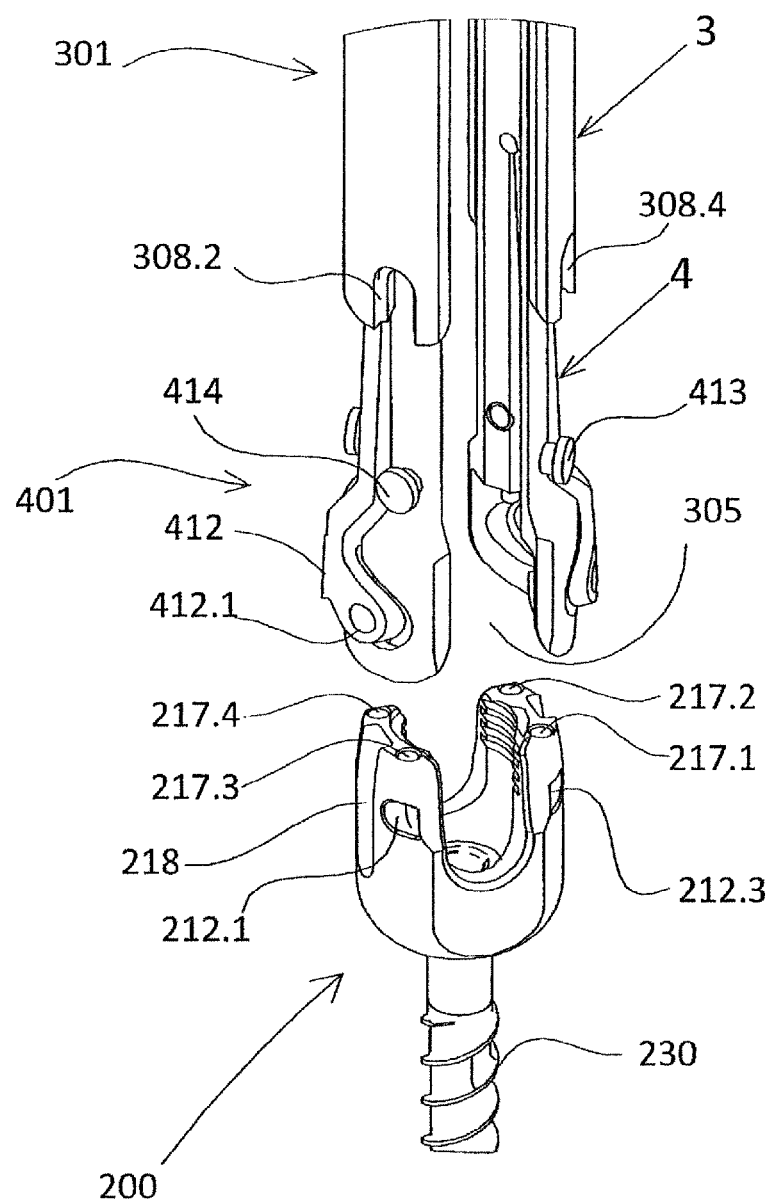
FIGS. 3A, 3B and 4 are partial side front elevational views of the present invention in the open configuration.
Figure 3B:
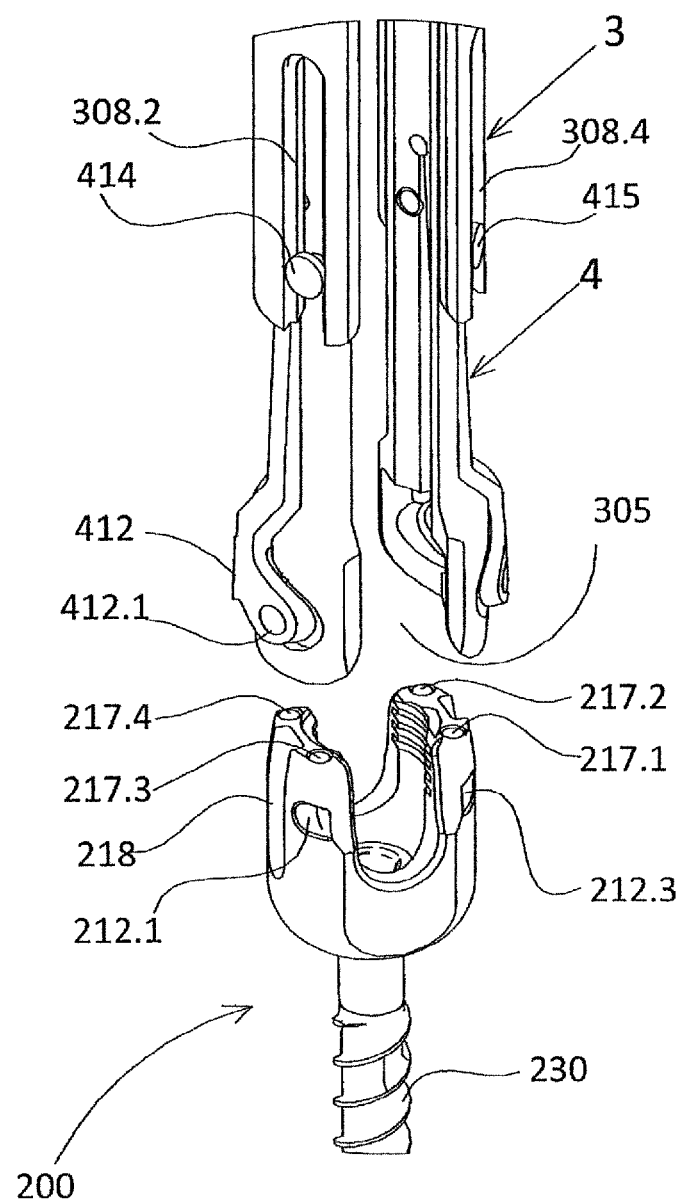
Figure 4:
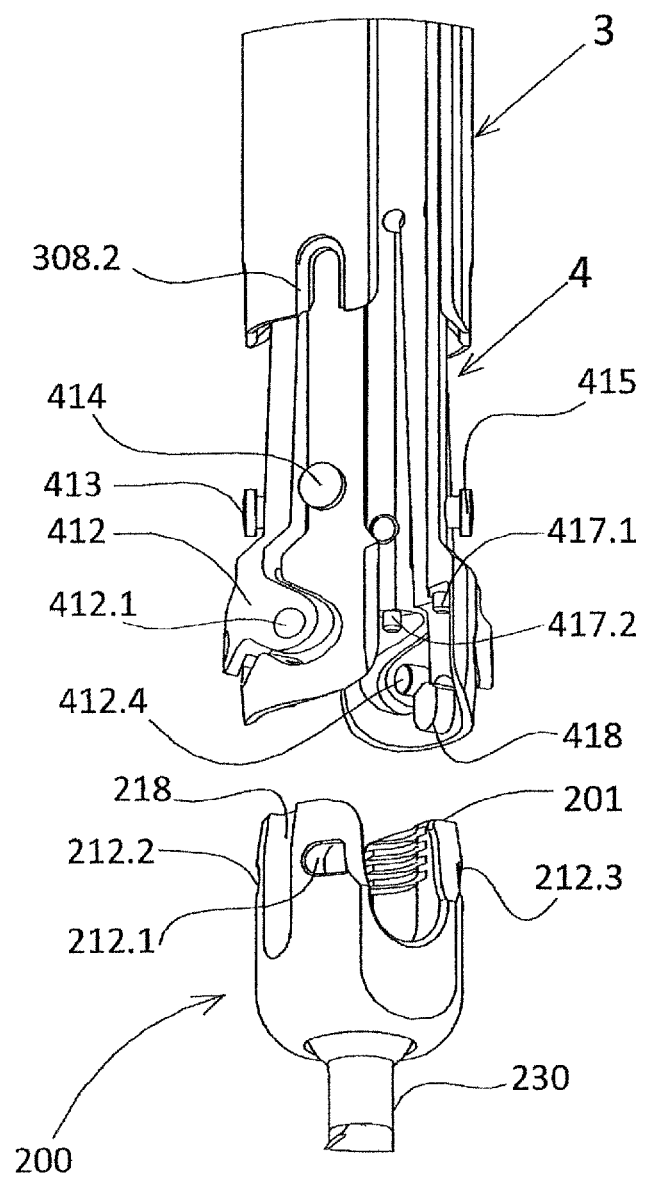

In FIG. 2 is shown an exploded view of the device 100 for implanting a surgical screw 2 disassembled into its main parts. It includes an outer sleeve 3, having a substantially cylindrical shape, with a hollow interior, having a hollow outer central body 303 and two end parts, in turn with a hollow interior, and integrally connected to it: a first part of the outer end 301, the proximal outer, which has a substantially circular section and the open bottom, in communication with the internal cavity of the outer central body 303 and an outer distal part 302, the outer distal part 302 having circular hollow section and the open top, in communication with the internal cavity of the outer central body 303. With reference to FIGS. 3A-3B, it is possible to identify two windows 306 and 307 located in part in the part of outer distal end 302 (hereinafter outer distal part) and in part in the upper part of the outer central body 303. Again with reference to the FIGS. 3A-3B, starting from the first part of outer proximal end 301 (hereinafter outer proximal part), there are two passing through external channels 304 and 305, which extend throughout the length of the outer proximal part 301 and for substantial part of the outer central body 303, in axial opposition to each other. Additionally, the outer proximal part 301 has, in its terminal part, a coupling edge 308. The coupling edge 308 of the outer proximal part 301 has provided with retaining elements, for example, two pairs of passing through, axial channels 308.1 and 308.2, 308.3 and 308.4 (FIGS. 2-8B), arranged along the circumference of the coupling edge 308. The first pair of channels 308.1 and 30.2 is divided from the second pair of channels 308.3 and 308.4 by the two external channels 304 and 305, which, as mentioned, branch off from the coupling edge 308 dividing it into two equal circular rings on which lie the two the pairs of channels 308.1 and 308.2, 308.3 and 308.4.

Again with reference to FIG. 2, the device 100 for implanting a surgical screw 2 also comprises an inner sleeve 4 having a cylindrical shape, a vertical axis and an axial cavity, extending in the axial direction and having axial dimensions greater than the outer sleeve 3 and a lower diameter of the outer sleeve 3. The dimensions are such as to allow the outer sleeve 3 to accommodate, in its axial cavity, a substantial part of the inner sleeve 4. The inner sleeve 4 comprises: an inner central body 403, having a substantially cylindrical shape, a hollow interior and shaped so as to be received in the axial cavity of the outer sleeve 3 and to be mated with the structural features. To the inner central body 403 are integrally connected two end parts with a hollow interior: a first inner proximal end part 401, the inner proximal part, and an inner distal end part 402, the inner distal part, being the inner proximal and inner distal part 401 and 402 integrally connected to the inner central body 403 so that the respective hollow interiors are in communication to each other.

The central body 403 has two internal inner channels 404 and 405 passing through and extending axially for a substantial part of the inner central body 403 and for the total inner proximal part 401. The two inner channels 404 and 405, mutually axially positioned, have position and shape such as to overlap with the above external channels 304 and 305 on the outer sleeve 3 so that, when the device 100 is in the assembled configuration, the overlap of the outer channel 304 with the inner channel 404 and the overlap of the outer channel 305 with the inner channel 405 are in the channels 104 and 105 of FIGS. 1A-1B and 6.

Figure 6:
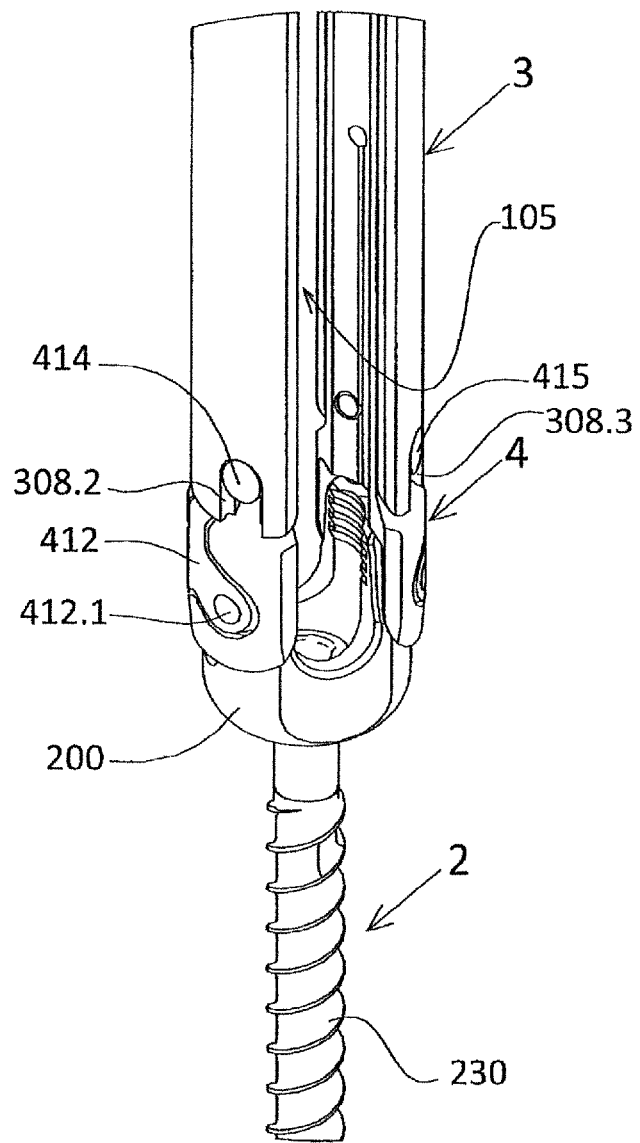
FIGS. 6 and 7A are partial views of the present invention in combination with a polyaxial screw in the closed configuration.

The inner proximal part 401 is divided into two end portions 411 and 421 from the two inner channels 404 and 405. The two end portions 411 and 421, as can be seen in the attached drawing, have the same structural and functional characteristics, and therefore only one (411) of the two (411, 421) portions will be described. The first end portion 411 has, on its outer surface, a lateral engagement device 412 and two stop elements, for example, a pair of outer side coupling pins 413 and 414 are projecting from an outer surface of the substantially mushroom-shaped inner proximal part 401. The two pairs of outer side pins 413, 414 and 415, 416 perform both a stop function during the sliding of the outer sleeve along the inner sleeve, during the transition from the closed configuration to the open configuration, and a retaining function when the device is in the closed configuration with respect to any bending stresses that could misalign the outer sleeve 3 with respect to the inner sleeve 4, resulting in the accidental and unintended opening of the device 100, thereby causing the loss of grip of the device 100 on the polyaxial screw 2. The lateral engagement device 412 is formed from the inner proximal part 401 by, for example, cutting and bending towards the outside of a part of the outer surface of the portion 411. The lateral engagement device 412 is configured in the peninsula as respect to the end portion 411 and is integrally connected to it by means of its upper side only 412.3, while for the remaining three sides it protrudes from the end portion 411 radially and for a substantial part of its length. Due to the shape just described, the lateral engagement device 412 is able to move between a free configuration (FIG. 2), in which the lateral engagement device 412 protrudes radially from the inner proximal part 401, and an engagement configuration (FIG. 6). The lateral engagement device 412 is aligned with the outer surface of the inner proximal part 401.

At the sides of the lateral engagement device 412 is located the pair of outer side coupling pins 413 and 414, one for each side of the lateral engagement device 412, also projecting from the outer surface of the inner proximal part 401. On the inner face of the lateral engagement device 412 facing towards the axial cavity of the inner sleeve 4, coupling elements are provided, for example, two radial pins 412.1 and 412.2, integral with respect to the lateral engagement device 412 and projecting towards the axial cavity of the inner sleeve 4. These two inner radial pins 412.1 and 412.2 are located at the side of the lateral engagement device 412 distal to the upper side 412.3 of the lateral engagement device 412.

Figure 5:
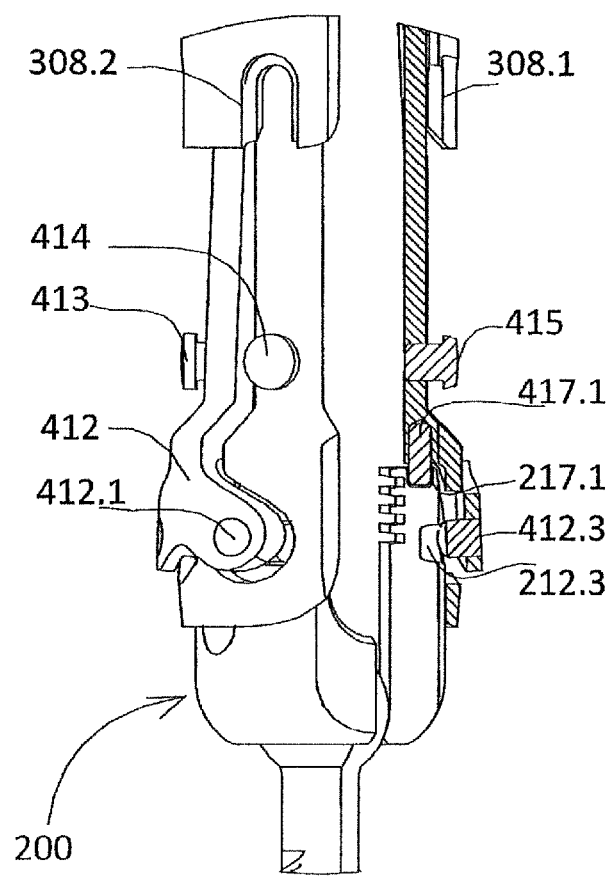
FIG. 5 is a partial view of the present invention in combination with polyaxial screw in the open configuration shown as a partial section.
Figures 7A, 7B:
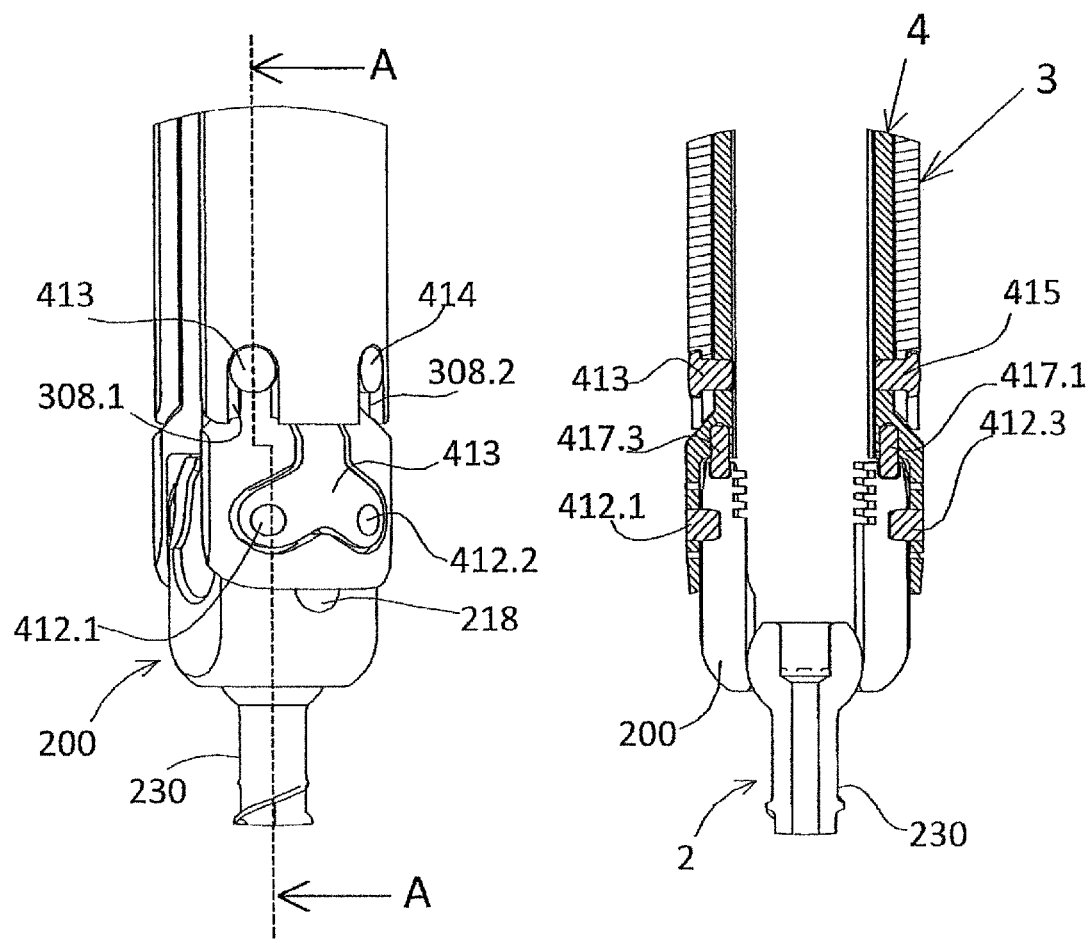
FIG. 7B is a sectional view along the line A-A shown in FIG. 7A.
Figures 8A, 8B:
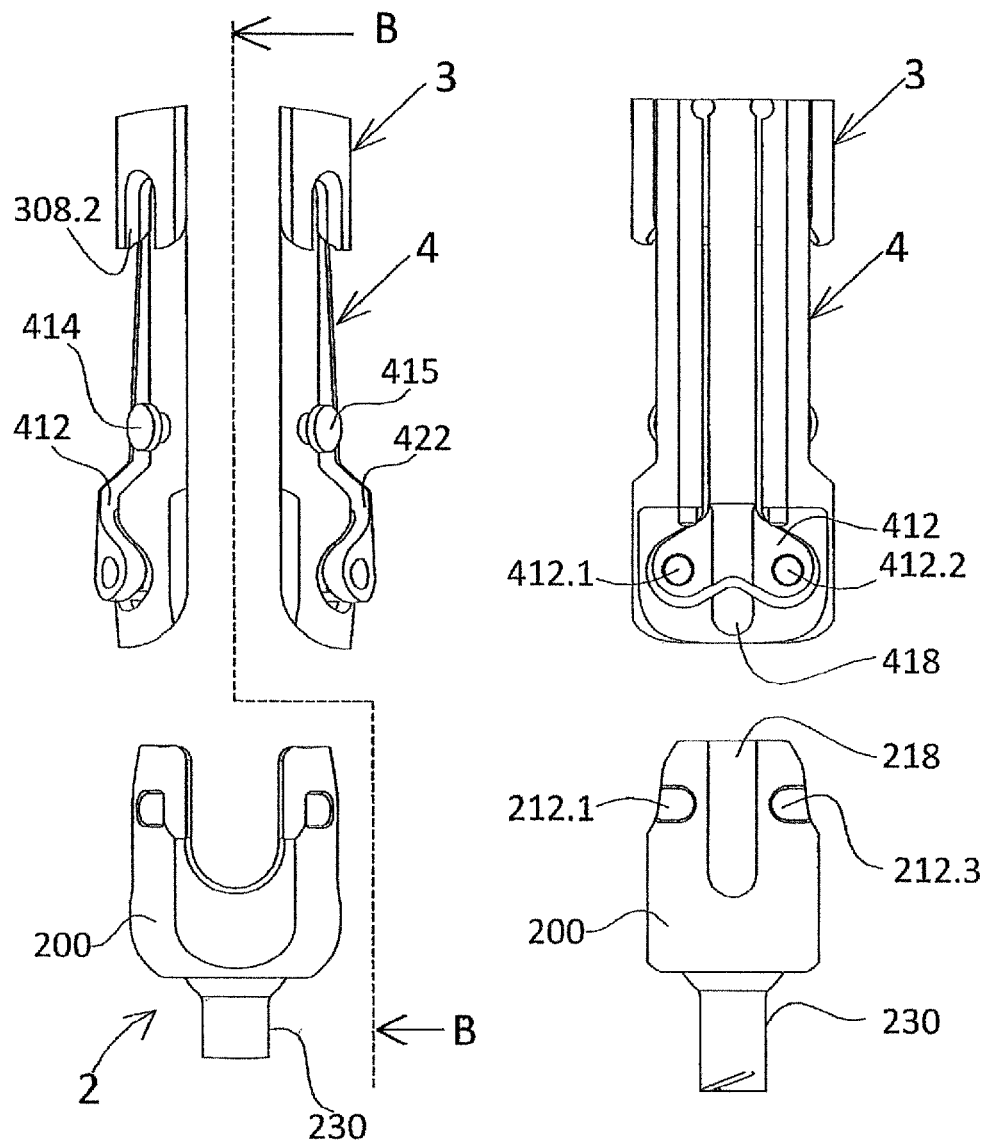
FIG. 8A is a partial side elevational view of the present invention in the open configuration.
FIG. 8B is a cross-sectional view taken along the line B-B in FIG. 8A.

As can be appreciated from FIGS. 5 and 7A-7B, in the inner portion of the inner sleeve 4, there are the axial engagement elements, for example two pairs of axial pins 417.1, 417.2 and 417.3, 417.4. The pairs of inner axial pins 417.1, 417.2 and 417.3, 417.4 have an axis normal to the central axis of the inner sleeve 4 and extend longitudinally in the axial direction.

Close to the entrance of the two end portions 411 and 421 (FIG. 4), on each of them there is an alignment element, for example a respective alignment protrusion 418. The alignment protrusion 418 is shaped so as to be received in a respective cavity 218 made in the head part 200 of the polyaxial screw 2. When, during the coupling between the polyaxial screw 2 and the present invention 100, the polyaxial screw 2 is received within the proximal part 401 of the inner sleeve 4, the pair of alignment protrusions 418 (one for each end portion 411 and 421), fitting down in the respective cavity 218, ensures the proper alignment between the inner sleeve 4 and the polyaxial screw 2.

The outer distal part 402 has, in its part adjacent to the inner central body 403, a passing through opening 406, which overlooks the inner axial cavity. Jutting cantilevered on the window 406 is a button 420 supported by a bridge 431 which branches off from the inner central body 403 and overlooking the window 406. The button 420 is elastically movable between a neutral position, coplanar to the outer surface of the inner central body 403, and a retracted position, in which the button 420 engages the central axial cavity of the inner sleeve 4.

In the opened assembled configuration, as can be seen in FIG. 1B, the device 100 for implanting a surgical screw 2 has the outer sleeve 3 fitted on the inner sleeve 4; the inner proximal part 401 of the inner sleeve 4 comes out, for almost all of its length, from the outer proximal part 301 of the outer sleeve 3. Moreover, the lateral engagement devices 412 and 422 are in the free configuration, i.e. both projecting from the outer surface of the inner proximal part 401. The button 420 occupies the window 306 while the window 307 is empty.

Operation when the device 100 for implanting a surgical screw 2 is in the open configuration of FIG. 1B, the operation provides the insertion of the polyaxial screw 2 within the portion of the axial cavity included in the inner proximal part 401. The polyaxial screw 2 is typical in the art and is described herein only in the substantial aspects in order to better illustrate the operation of the device 100 subject matter of the present invention. The polyaxial screw 2 comprises a head part 200 and a threaded shank 230. At the top 201 of the head part 200 of the polyaxial screw 2 (FIGS. 3A-3B), there are two pairs of axial channels 217.1, 217.2 and 217.3, 217.4. Also, in the head part 200, from the side with respect to the axis of the threaded shank 230 of the polyaxial screw 2 (FIGS. 2, 3A, 3B, 4), there are the coupling parts, for example two pairs of side channels 212.1, 212.2 and 212.3, 212.4. When the polyaxial screw 2 is coupled with the device 100 for implanting a surgical screw 2, the head part 200 of the polyaxial screw 2 is, as mentioned, partially received within the proximal internal part 401 of the inner sleeve 4, thus allowing two pairs of inner axial pins 417.1, 417.2 and 417.3, 417.4 to engage the two pairs of axial channels 217.1, 217.2 and 217.3, 217.4, respectively. This coupling makes the polyaxial screw 2 and the device 100 for implanting a surgical screw integral with respect to a possible rotation along the central axis of the device 100 itself.

Then, by pressing the button 420 in the direction normal to the central axis of the device 100, the button 420 moves inward to engage the axial cavity of the inner sleeve 4 freeing the window 306. This translational movement of the button 420 towards the inside of the device 100 allows the user to slide the outer sleeve 3 axially along the inner sleeve 4 in the direction of the polyaxial screw 2. Through this sliding, the button 420, shifted towards the inside of the device 100, passes under the divider section 310 to engage the window 307 once the sliding is complete. During the sliding of the outer sleeve 3 with respect to the inner sleeve 4 in the direction of the polyaxial screw 2, the outer proximal part 301 descends along the inner proximal part 401 until the two pairs of outer side coupling pins 413, 414 and 415, 416 not engage the channels 308.3, 308.4 and 308.1, 308.2, as shown in FIG. 6, respectively.

As can be appreciated from FIGS. 5 and 6, the lateral engagement devices 412 and 422, precisely because of the action exerted by the outer proximal part 301 on them, vary their position from a projecting position with respect to the outer surface of the inner proximal part 401 (FIG. 5) to a longitudinally aligned position with respect to the outer surface of the inner proximal part 401. In this way, the two pairs of inner radial pins 412.1, 412.2 and 412.3, 412.4 engage the two pairs of side channels 212.1, 212.2 and 212.3, 212.4. In this way, the polyaxial screw 2 becomes integral with respect to the device 100 for implanting a surgical screw 2, reaching the closed configuration of the device 100 for implanting a surgical screw 2.

In this configuration, reached at a complete sliding of the outer sleeve 3 on the inner sleeve 4, the button 420 regains neutral position engaging the window 307, thus blocking the device 100 of the present invention in the closed configuration and being coupled to the polyaxial screw 2. When the top 110 at the distal end part 102 is open, it is possible to access the internal cavity of the device 100 until reaching the polyaxial screw 2. In this way, one can act on it in order to secure it in a suitable location or to perform necessary procedures during an implantation.

Furthermore, the channels 104 and 105 (FIGS. 1A-1B and 6), made by the overlapping of the pairs of through outer 304, 305 and inner channels 404, 405, respectively, are available for the insertion of a bar (not shown) adapted to be secured to the head of the polyaxial screw 2 according to a technology known in the art and not further illustrated. After completing the necessary procedures for implanting the polyaxial screw 2, by pressing the button 420 and by moving it from its neutral position, one can slide the outer sleeve 3 along the inner sleeve 4 bringing the device 100 in the open configuration and freeing so the polyaxial screw 2 just implanted.

As is appreciated by those skilled in the art, the present embodiments advantageously achieve the objectives listed above by solving the drawbacks of the known state of the art. Of course, numerous variations may be made in practice with respect to those described and illustrated by way of non-limiting example, without thereby departing from the scope of the present invention and, therefore, from the domain of the present industrial property right.

The invention claimed is:

1. A device for implanting a surgical screw comprising:
an outer sleeve; and
an inner sleeve configured to couple axially and slidingly with said outer sleeve;
said outer sleeve comprising
an outer proximal end part,
an outer distal end part opposing said outer proximal end part, and
at least one outer channel extending along said outer proximal end part;
said inner sleeve comprising
an inner proximal end part,
an inner distal end part opposing said inner proximal end part, and
at least one inner channel extending along said inner proximal end part;
said inner proximal end part comprising
first and second end portions defined by said at least one inner channel,
first and second lateral engagement elements each comprising a distal end, a proximal end, and first and second opposing sides between said distal end and said proximal end,
said first and second lateral engagement elements being respectively integral with said first and second end portions,
each of said first and second lateral engagement elements configured to switch between
a free position, and
an engagement position,
and
first and second pairs of inner axial pins respectively extending from said first and second end portions, the first and second pairs of inner axial pins configured to engage a top of the surgical screw, and
first and second pairs of inner radial pins respectively extending from said first and second lateral engagement elements, the first and second pairs of inner radial pins being transverse to a longitudinal axis of said inner sleeve and the first and second pairs of inner axial pins, the first and second pairs of inner radial pins configured to engage a side of the surgical screw.

2. The device as claimed in claim 1 wherein each of said first and second lateral engagement elements is free to move between the free position and the engagement position.

3. The device as claimed in claim 2 wherein each of the first and second lateral engagement elements is moved between the free position and the engagement position via the outer sleeve acting on said first and second lateral engagement elements.

4. The device as claimed in claim 3 wherein said outer sleeve slides on at least a part of the inner sleeve so as to act on said first and second lateral engagement elements.

5. The device as claimed in claim 3 wherein said inner sleeve comprises a control element configured to cooperate with the outer sleeve to act on said first and second lateral engagement elements.

6. The device as claimed in claim 3 wherein the surgical screw is secured to the inner proximal end part through engagement by the first and second lateral engagement elements, said engagement being controlled by relative movement of the outer sleeve with respect to the inner sleeve.

7. The device as claimed in claim 1 further comprising at least one retaining element configured to receive at least one stop element when in the engagement position.

8. The device as claimed in claim 7 wherein said at least one stop element has a free end having a diameter greater than a characteristic dimension of the respective at least one retaining element so as to prevent said at least one stop element from leaving its respective at least one retaining element.

9. The device as claimed in claim 1 wherein the inner proximal end part comprises at least one alignment element configured to engage with at least one respective cavity of the surgical screw.

10. A device for implanting a surgical screw comprising:
an outer sleeve with a hollow interior; and
an inner sleeve with a hollow interior and configured to couple axially and slidingly with said outer sleeve;
said outer sleeve comprising
an outer central body, an outer proximal end part,
an outer distal end part integrally connected with said outer proximal end part, said outer central body being between said outer proximal end part and said outer distal end part, and
at least one outer channel extending along an entirety of said outer proximal end part and along at least a part of said outer central body;
said inner sleeve comprising
an inner central body,
an inner proximal end part,
an inner distal end part integrally connected with said inner proximal end part, said inner central body being between said inner proximal end part and said inner distal end part, and
at least one inner channel extending along an entirety of said inner proximal end part and along at least part of the inner central body,
said inner proximal end part comprising
first and second end portions defined by said at least one inner channel,
first and second lateral engagement elements each comprising a distal end, a proximal end, and first and second opposing sides between said distal end and said proximal end,
said first and second lateral engagement elements being respectively integral with said first and second end portions,
each of said first and second lateral engagement elements configured to switch between
a free position, and
an engagement position,
first and second pairs of inner axial pins respectively extending from said first and second end portions, the first and second pairs of inner axial pins configured to engage a top of the surgical screw, and
first and second pairs of inner radial pins respectively extending from said first and second lateral engagement elements, the first and second pairs of inner radial pins being transverse to a longitudinal axis of said inner sleeve and the first and second pairs of inner axial pins, the first and second pairs of inner radial pins configured to engage a side of the surgical screw.

11. The device for implanting a surgical screw as claimed in claim 10, wherein each of said first and second lateral engagement elements is free to move between the free position and the engagement position.

12. The device for implanting a surgical screw as claimed in claim 11, wherein each of said first and second lateral engagement elements is moved between the free position and the engagement position via the outer sleeve acting on said first and second lateral engagement elements.

13. The device for implanting a surgical screw as claimed in claim 12, wherein said outer sleeve slides on at least a part of the inner sleeve so as to act on said first and second lateral engagement elements.

14. The device for implanting a surgical screw as claimed in claim 12, wherein said inner sleeve comprises a control element configured to cooperate with the outer sleeve to act on said first and second lateral engagement elements.

15. The device for implanting a surgical screw as claimed in claim 12 wherein the surgical screw is secured to the inner proximal end part through engagement by the first and second lateral engagement elements, said engagement being controlled by relative movement of the outer sleeve with respect to the inner sleeve.

16. The device for implanting a surgical screw as claimed in claim 10, further comprising at least one retaining element configured to receive at least one stop element when in the engagement position.

17. The device for implanting a surgical screw as claimed in claim 16, wherein said at least one stop element has a free end having a diameter greater than a characteristic dimension of the respective at least one retaining element so as to prevent said at least one stop element from leaving its respective at least one retaining element.

18. The device for implanting a surgical screw as claimed in claim 10 wherein the inner proximal end part comprises at least one alignment element configured to engage with at least one respective cavity of the surgical screw.

* * * * *